(12) United States Patent
Fujimori

(10) Patent No.: US 9,281,423 B2
(45) Date of Patent: Mar. 8, 2016

(54) IMAGE PICKUP APPARATUS, ENDOSCOPE AND IMAGE PICKUP APPARATUS MANUFACTURING METHOD

(71) Applicant: OLYMPUS CORPORATION, Tokyo (JP)

(72) Inventor: Noriyuki Fujimori, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 398 days.

(21) Appl. No.: 13/747,806

(22) Filed: Jan. 23, 2013

(65) Prior Publication Data

US 2013/0128020 A1 May 23, 2013

Related U.S. Application Data

(63) Continuation of application No. PCT/JP2011/062956, filed on Jun. 6, 2011.

(30) Foreign Application Priority Data

Jul. 23, 2010 (JP) ................................. 2010-166009

(51) Int. Cl.
*H04N 7/18* (2006.01)
*H01L 31/0232* (2014.01)
*A61B 1/00* (2006.01)
(Continued)

(52) U.S. Cl.
CPC ...... *H01L 31/02327* (2013.01); *A61B 1/00096* (2013.01); *A61B 1/05* (2013.01); *A61B 1/051* (2013.01); *H01L 27/14618* (2013.01); *H01L 27/14625* (2013.01); *H01L 31/02325* (2013.01); *H01L 31/18* (2013.01); *H04N 5/2254* (2013.01);
(Continued)

(58) Field of Classification Search
CPC ...... A61B 1/00096; A61B 1/05; A61B 1/051; A61B 1/042; A61B 1/045; H01L 27/14618; H01L 27/14625; H01L 31/02325; H01L 31/02327; H01L 31/18; H04N 2005/2255; H04N 5/2254; H04N 7/183
USPC ........................................................... 348/65
See application file for complete search history.

(56) References Cited

U.S. PATENT DOCUMENTS 8,208,047 B2 * 6/2012 Schultz .......................... 348/262
2002/0075391 A1 * 6/2002 Shizukuishi .................. 348/319
(Continued)

FOREIGN PATENT DOCUMENTS

| EP | 1 376 705 A2 | 1/2004 |
|---|---|---|
| JP | 3-279908 A | 12/1991 |

(Continued)

OTHER PUBLICATIONS

Extended Supplementary European Search Report dated Jun. 26, 2014 from related European Application No. 11 809500.9.

*Primary Examiner* — Shan Elahi
(74) *Attorney, Agent, or Firm* — Scully, Scott, Murphy & Presser, P.C.

(57) ABSTRACT

An image pickup apparatus includes: a cover glass portion having a function of a right angle prism; an image pickup device substrate portion including an image pickup device on a first principal surface and a back-face electrode on a second principal surface, the back-face electrode being connected to the image pickup device via a through-wiring; and a bonding layer that bonds the cover glass portion and the image pickup device substrate portion that have a same outer dimension.

6 Claims, 5 Drawing Sheets

(51) Int. Cl.
  *A61B 1/05* (2006.01)
  *H01L 27/146* (2006.01)
  *H04N 5/225* (2006.01)
  *H01L 31/18* (2006.01)

(52) U.S. Cl.
  CPC ........ *H04N 7/183* (2013.01); *H01L 2924/0002* (2013.01); *H04N 2005/2255* (2013.01)

(56) References Cited

U.S. PATENT DOCUMENTS

| | | | |
|---|---|---|---|
| 2004/0130640 A1 | 7/2004 | Fujimori | |
| 2006/0055793 A1* | 3/2006 | Adler et al. | 348/211.99 |
| 2007/0002135 A1* | 1/2007 | Glukhovsky | 348/77 |
| 2007/0177009 A1* | 8/2007 | Bayer et al. | 348/65 |
| 2008/0055536 A1* | 3/2008 | Shimozono et al. | 349/200 |
| 2009/0046183 A1* | 2/2009 | Nishida et al. | 348/294 |
| 2009/0053850 A1* | 2/2009 | Nishida et al. | 438/64 |
| 2010/0085466 A1* | 4/2010 | Fujimori et al. | 348/340 |
| 2011/0157446 A1* | 6/2011 | Kasai et al. | 348/308 |

FOREIGN PATENT DOCUMENTS

| | | |
|---|---|---|
| JP | 4-248501 | 9/1992 |
| JP | 6-229825 | 8/1994 |
| JP | 8-116042 | 5/1996 |
| JP | 11-352413 | 12/1999 |
| JP | 2000-125161 A | 4/2000 |
| JP | 2002-45333 | 2/2002 |
| JP | 2003-204053 | 7/2003 |
| JP | 2009-210874 A | 9/2009 |
| JP | 2010-093200 | 4/2010 |
| WO | WO 2010/041579 A1 | 4/2010 |

\* cited by examiner

IMAGE PICKUP APPARATUS, ENDOSCOPE AND IMAGE PICKUP APPARATUS MANUFACTURING METHOD

CROSS REFERENCE TO RELATED APPLICATION

This application is a continuation application of PCT/JP2011/062956 filed on Jun. 6, 2011 and claims benefit of Japanese Application No. 2010-166009 filed in Japan on Jul. 23, 2010, the entire contents of which are incorporated herein by this reference.

BACKGROUND OF THE INVENTION

1. Field of the Invention

The present invention relates to an image pickup apparatus, an endoscope and an image pickup apparatus manufacturing method, and specifically relates to an image pickup apparatus manufactured by wafer-level chip-size packaging, an endoscope including the image pickup apparatus and a method for manufacturing the image pickup apparatus.

2. Description of the Related Art

Electronic endoscopes, camera-equipped mobile phones and digital cameras, etc., that include an image pickup apparatus including a solid-state image pickup device such as a CCD or a CMOS have widely been used. An image pickup apparatus includes an image pickup device substrate portion with a solid-state image pickup device formed thereon, and a cover glass portion that protects the solid-state image pickup device.

Image pickup apparatus manufacturing methods using wafer-level chip-size packaging (WL-CSP) for downsizing and mass production of image pickup apparatuses are known. For example, Japanese Patent Application Laid-Open Publication No. 2003-204053 discloses a method in which a semiconductor wafer with a large number of image pickup devices formed thereon and, e.g., a glass substrate are bonded and the resulting semiconductor wafer is subsequently cut for singulation to obtain a large number of image pickup apparatuses in a batch.

Also, Japanese Patent Application Laid-Open Publication No. 2002-45333 discloses a horizontal image pickup apparatus that shoots an object in a direction perpendicular to an image pickup device surface. For horizontal image pickup apparatuses, a step of bonding a right angle prism to an upper face of a cover glass is necessary.

SUMMARY OF THE INVENTION

An image pickup apparatus according to an embodiment of the present invention includes: a transparent substrate portion including an optical path conversion element function portion; an image pickup device substrate portion including an image pickup device on a first principal surface and a back-face electrode on a second principal surface, the back-face electrode being connected to the image pickup device via a wiring portion; and a bonding layer that bonds the transparent substrate portion and the image pickup device substrate portion that have a same outer dimension.

Also, an endoscope according to another embodiment of the present invention includes: an image pickup optical system including a plurality of lens portions; an image pickup apparatus including a transparent substrate portion including an optical path conversion element function portion, an image pickup device substrate portion including an image pickup device on a first principal surface and a back-face electrode on a second principal surface, the back-face electrode being connected to the image pickup device via a wiring portion, and a transparent substrate portion having an outer dimension equal to an outer dimension of the image pickup device substrate portion and being bonded to the image pickup device substrate portion via a bonding layer; and a barrel portion.

Also, a method for manufacturing an image pickup apparatus according to still another embodiment of the present invention, the method including: an image pickup device substrate fabricating step of fabricating an image pickup device substrate including a plurality of image pickup devices on a first principal surface and a plurality of back-face electrodes on a second principal surface, the plurality of back-face electrodes being connected to the respective image pickup devices via respective wiring portions; a bonded substrate fabricating step of fabricating a bonded substrate by bonding a transparent substrate to the first principal surface of the image pickup device substrate via a bonding layer; a prism fabricating step of fabricating an optical path conversion element by forming a groove portion in the transparent substrate on the image pickup devices, the groove portion including a perpendicular surface perpendicular to the first principal surface and an inclined surface inclined relative to the first principal surface; and a singulation step of singulating the bonded substrate into individual image pickup apparatuses.

DETAILED DESCRIPTION OF THE PREFERRED EMBODIMENT

<First Embodiment>

Figure 1:
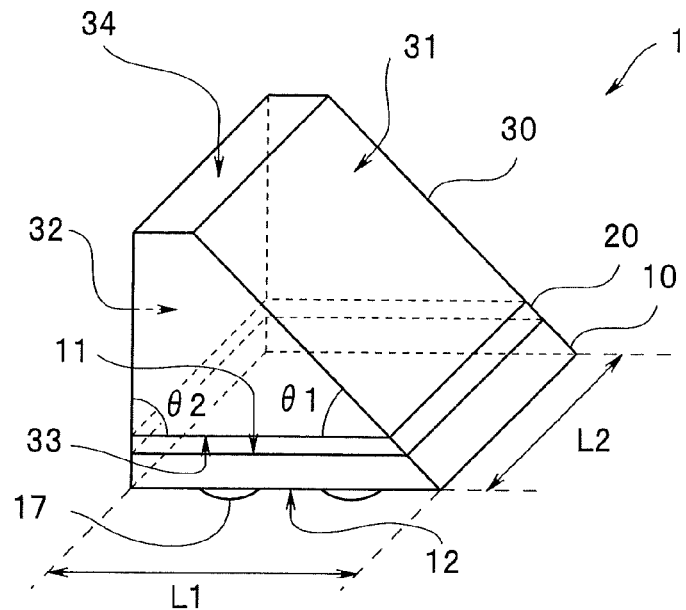
FIG. 1 is an outer appearance diagram of an image pickup apparatus according to a first embodiment.
Figure 2:
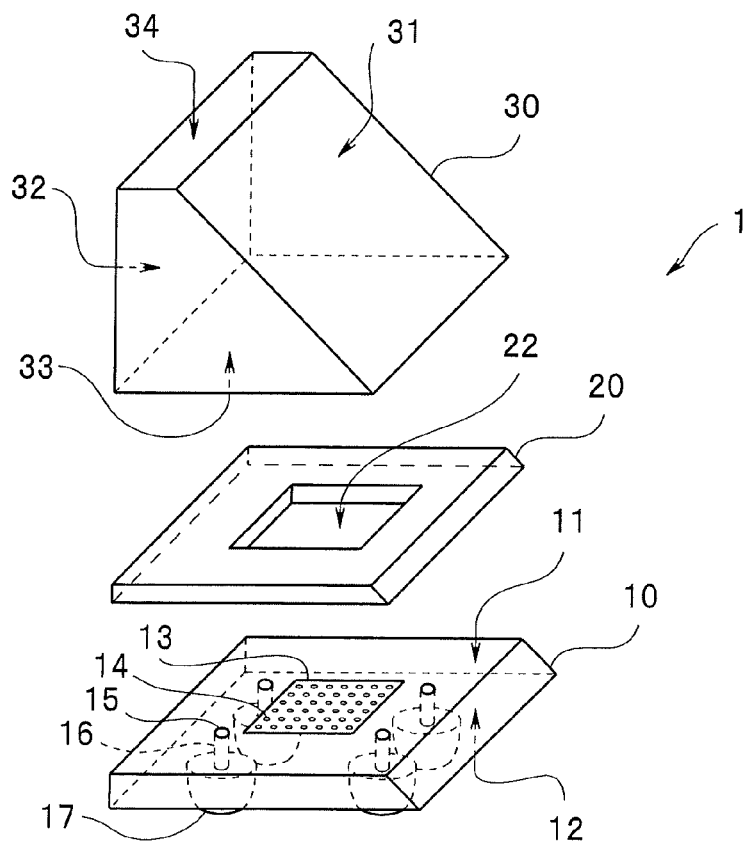
FIG. 2 is an exploded view of the image pickup apparatus according to the first embodiment.

An image pickup apparatus 1 according to a first embodiment of the present invention and a method for manufacturing the image pickup apparatus 1 will be described below with reference to the drawings. First, a structure of the image pickup apparatus 1 according to the present embodiment will be described. As illustrated in FIGS. 1 and 2, the image pickup apparatus 1 includes an image pickup device substrate portion 10, a bonding layer 20 and a cover glass portion 30, which is a transparent substrate portion. The image pickup apparatus 1 is of a horizontal type, and a light beam incident on a perpendicular surface 32 of the cover glass portion 30 from the left side in the diagram in FIG. 1 is reflected by an inclined surface 31 and reaches an image pickup device 13 via a lower face 33.

As described later, the image pickup apparatus 1 is manufactured by wafer-level chip-size packaging. In other words, a large number of image pickup apparatuses are manufactured in a batch at the stage of a wafer and then the wafer is singulated into individual chips (image pickup apparatuses) by means of cutting (dicing) processing. Thus, as illustrated in FIG. 1, outer dimensions (dimensions of a surface where an image pickup device is formed) of each of the image pickup device substrate portion 10, the bonding layer 20 and the cover glass portion 30 are outer dimensions, i.e., L1 and L2, of the image pickup apparatus 1. In other words, respective outer dimensions (bottom face dimensions) of the image pickup device substrate portion 10, the bonding layer 20 and the cover glass portion 30 as observed from above are the same. Note that since in the image pickup apparatus 1, the image pickup device substrate portion 10 and the cover glass portion 30 have respective side faces with a same inclination angle θ1, respective outer dimensions in an L1 direction of the image pickup device substrate portion 10, the bonding layer 20 and the cover glass portion 30 are slightly different from one another to be exact. However, since the difference is slight, the respective outer dimensions of the device substrate portion 10 and the cover glass portion 30 are regarded as being the same.

The image pickup device substrate portion 10 includes the image pickup device 13 on a first principal surface 11 and back-face electrodes 17 on a second principal surface 12, the back-face electrodes 17 being connected to the image pickup device 13 via through-wirings 16, which are wiring portions. The through-wirings 16 are connected to the image pickup device 13 via front-face electrodes 15 and front-face wirings (not illustrated). On an upper face of the image pickup device 13, a number of microlenses 14, the number being equal to a number of pixels, are formed.

The cover glass portion 30 has a protection member function that protects the image pickup device 13. Furthermore, in the image pickup apparatus 1, the cover glass portion 30 includes the perpendicular surface 32 perpendicular to the first principal surface 11 of the image pickup device substrate portion 10 and an inclined surface 31 inclined by 45 degrees relative to the first principal surface 11 of the image pickup device substrate portion 10, and is an optical path conversion element function portion that converts a path of incident light and makes the light exit in a direction different from an incident direction. In other words, in FIG. 1, θ1=45 degrees and θ2=90 degrees, and the cover glass portion 30 provides a right angle prism. The inclined surface 31 is a reflective surface of the right angle prism, and as already described, a light beam entering from the perpendicular surface 32 is reflected by the inclined surface 31, resulting in an optical path of the light beam being converted by 90 degrees, whereby the light beam enters the image pickup device 13.

Furthermore, the bonding layer 20 that bonds the cover glass portion 30 to the image pickup device substrate portion 10 is provided in such a manner that an air gap 22 is formed above a region of the image pickup device substrate portion 10 where the image pickup device is formed. In other words, between the region of the image pickup device substrate portion 10 where the image pickup device is formed and the cover glass portion 30, the air gap 22 is formed by the bonding layer 20 having a frame-like shape. In other words, the bonding layer 20 is not formed in the region where the image pickup device is formed.

Since the image pickup apparatus 1 is manufactured by WL-CSP, a cover glass portion that protects the image pickup device 13 is essential. As already described, since known horizontal image pickup apparatuses require a step of bonding a prism to each of image pickup apparatuses obtained as a result of singulation after the image pickup apparatuses are manufactured in a batch by WL-CSP, the productivity is sometimes not good. Furthermore, for image pickup apparatuses obtained by WL-CSP, a cover glass is essential for protecting an image pickup device. However, a dimension in a height direction (direction perpendicular to an image pickup element surface) of an image pickup apparatus is increased by the amount of a thickness of the cover glass. Thus, where a horizontal image pickup apparatus manufactured by WL-CSP is mounted in a distal end of an endoscope, the size of the distal end of the endoscope may be increased. However, in the image pickup apparatus 1, the cover glass portion 30 has a function as a right angle prism and thus, the image pickup apparatus 1 has a small size and provides good productivity.

Furthermore, in the image pickup apparatus 1 including the air gap 22, the microlenses 14 formed on the image pickup device 13 highly effectively collect light.

Next, a method for manufacturing the image pickup apparatus 1 will be described with reference to FIGS. 3 to 8.

<Image Pickup Device Substrate Fabricating Step>

An image pickup device substrate 10W including a plurality of image pickup devices 13 on a first principal surface 11 and a plurality of back-face electrodes 17 on a second principal surface 12, the plurality of back-face electrodes 17 being connected to the respective image pickup devices 13 via respective through-wirings 16, is fabricated.

The image pickup device substrate 10W includes, for example, a single-crystal silicon substrate, and on the first principal surface 11, the plurality of image pickup devices 13 are formed using a semiconductor circuit fabricating technique. Note that, although e.g., CCDs or CMOSs are preferably used as the image pickup devices, separately-manufactured image pickup device chips may be disposed on the image pickup device substrate 10W. On the respective image pickup devices 13, a number of microlenses, the number being equal to a number of pixels, are formed using, for example a transparent resin.

On the first principal surface 11 of the image pickup device substrate 10W, front-face electrodes 15, which are connected to front-face wirings (not illustrated) for power supply and signal transmission for the image pickup device 13, are formed. Then, the second principal surface 12 of the image pickup device substrate 10W is subjected to, e.g., dry etching processing or wet etching processing to form through-holes that reach back faces of the respective front-face electrodes 15. In other words, the through-holes are formed as via holes that extend through the single-crystal silicon substrate and include respective bottom portions formed by the respective front-face electrodes 15.

A conductor such as copper or aluminum is provided in respective inner portions and the bottom portions of the through-holes to form through-wirings 16, which are electrically connected to the respective front-face electrodes 15. Furthermore, back-face electrodes 17 connected to the respective through-wirings 16 are formed on the second principal surface 12. The back-face electrodes 17 are external connection electrodes for mounting, and are formed using, e.g., projecting copper bumps or solder balls.

Note that for the wiring portions connecting the image pickup device 13 of the first principal surface 11 and the back-face electrodes 17 of the second principal surface 12, side-face wirings may be used instead of the through-wirings 16.

Figure 3:
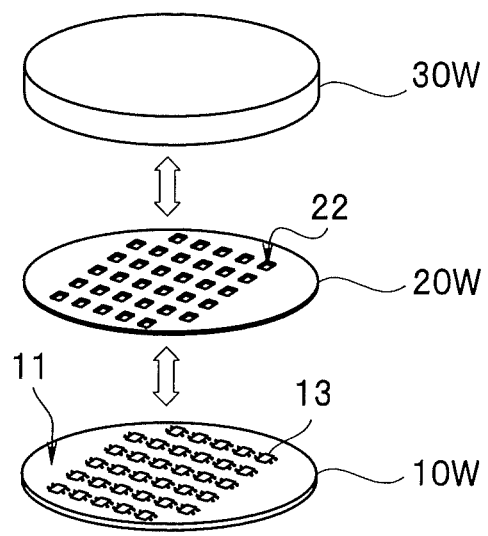
FIG. 3 is a diagram illustrating a bonded substrate fabricating step for the image pickup apparatus according to the first embodiment.

Note that although FIG. 3 indicates an example in which image pickup devices 13 are arranged in a grid of 6×6 on the image pickup device substrate 10W, in reality, image pickup devices 13 are arranged in a grid of 10×10 or more, and preferably in a grid of 20×20 or more.

<Bonded Substrate Fabricating Step>

Figure 4:
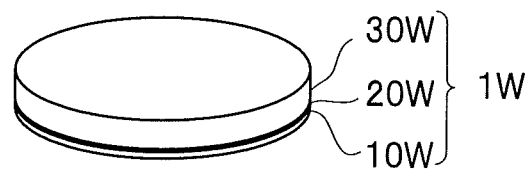
FIG. 4 is an outer appearance diagram illustrating a bonded substrate of the image pickup apparatus according to the first embodiment.

As illustrated in FIGS. 3 and 4, a glass substrate 30W, which is a transparent substrate, is bonded to the first principal surface 11 of the image pickup device substrate 10W via a bonding layer 20W to fabricate a bonded substrate 1W. Note that an antireflective film may be formed on a lower face 33 of the glass substrate 30W.

The bonding layer 20W is formed as a result of application of an adhesive bond in a pattern using, e.g., screen printing or ink-jetting. In other words, the adhesive bond is not applied to regions of the first principal surface 11 of the image pickup device substrate 10W where the image pickup devices are formed. The adhesive bond applied to regions in the peripheries of the image pickup devices except the regions where the image pickup devices are formed are subjected to curing processing after the lower face 33 of the glass substrate 30W are bonded to the adhesive bond. For the adhesive bond, an ultraviolet curable resin or a thermosetting resin may be used.

Note that although where the bonded substrate fabricating step is performed in a vacuum, no air exist in the air gap 22, which is a sealed space, the term "air gap" is used for convenience.

<Prism Fabricating Step (Separation Step)>

Figure 5:
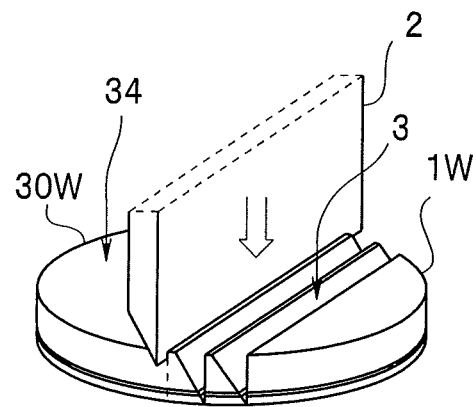
FIG. 5 is a perspective diagram illustrating a prism fabricating step for the image pickup apparatus according to the first embodiment.
Figure 6:
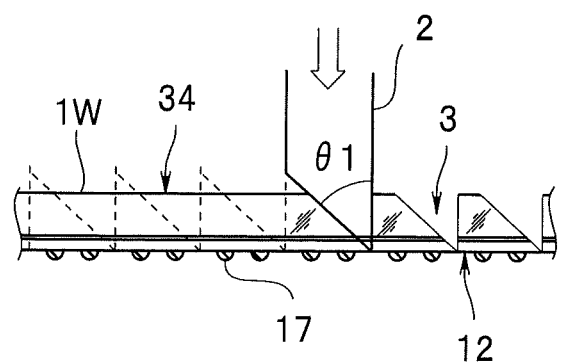
FIG. 6 is a cross-sectional structural diagram illustrating the prism fabricating step for the image pickup apparatus according to the first embodiment.

As illustrated in FIGS. 5 and 6, an upper face 34 of the glass substrate 30W on the image pickup device substrate 10W is subjected to dicing processing using a blade 2 with a bevel of 45 degrees ($\theta 1=45$ degrees) on one side to form groove portions 3 each including a perpendicular surface 32 perpendicular to the first principal surface 11 and an inclined surface 31 inclined relative to the first principal surface 11. In other words, a surface of the blade 2 where no bevel is formed is kept to have an angle of 90 degrees relative to the first principal surface 11 during the dicing processing. As a result of the formation of the groove portions 3 using the blade 2, the inclined surfaces 31 that serve as reflective surfaces of prisms and the perpendicular surfaces 32 that serve as light incident surfaces of the prisms are simultaneously formed. Although FIG. 5 indicates a blade including a straight cutting part for ease of illustration, it should be understood that normally, a circular blade, which is widely used in general, may be used.

Figure 7:
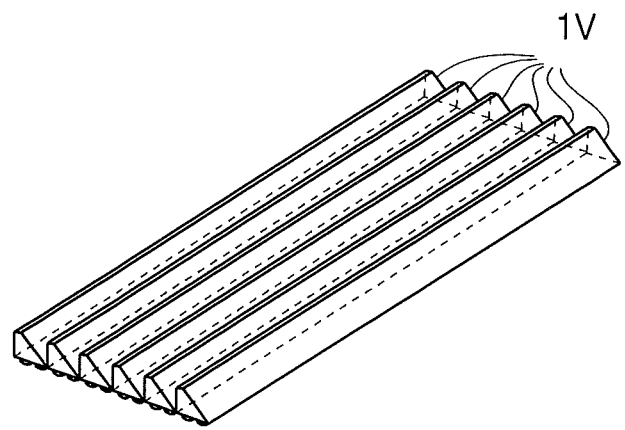
FIG. 7 is a perspective diagram illustrating the prism fabricating step for the image pickup apparatus according to the first embodiment.

Note that as illustrated in FIG. 7, in the method for manufacturing the image pickup apparatus 1 according to the present embodiment, in the prism fabricating step, simultaneously with the prism fabrication, the bonded substrate 1W is divided into rod-like substrates 1V each including a plurality of image pickup devices via the groove portions 3. In other words, bottom portions of the groove portions 3 reach the second principal surface 12 of the image pickup device substrate 10W.

<Grinding Step>

After the prism fabricating step, grinding processing of the inclined surfaces 31 of the bonded substrate 1W, which serve as the reflective surfaces of the prisms, and the perpendicular surfaces 32 of the bonded substrate 1W, which serve as the incident surfaces, is performed. This is because it is difficult to provide a flatness and a surface roughness acceptable for image pickup optical systems by the dicing processing using the blade 2 only. The grinding processing is performed until flat surfaces meeting optical specifications are provided, by a method using, e.g., a grinding solution that is similar to those used in normal prism grinding. The grinding processing is performed with reference to the second principal surface 12 on which the back-face electrodes 17 of the image pickup apparatuses 1 are formed, and an angle and a distance (plate thickness) between the first principal surface 11 and the second principal surface 12 are managed with high precision.

Figure 8:
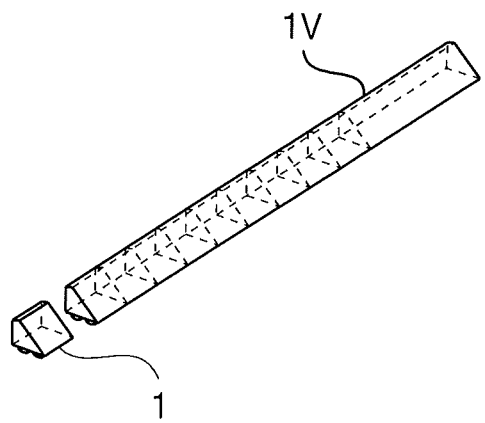
FIG. 8 is a perspective diagram illustrating a singulation step for the image pickup apparatus according to the first embodiment.

Although the grinding processing may be performed for each of the image pickup apparatuses after a singulation step, which will be described later, as illustrated in FIG. 8, it is preferable that the grinding processing be performed at the stage of the rod-like substrates 1V each including a row of image pickup apparatuses 1. The grinding processing of the rod-like substrates 1V is time-efficient and highly productive because processing of a plurality of image pickup apparatuses in a row is performed in a batch, and in addition, enables precisions in processing of prisms in the plurality of image pickup apparatuses to be managed to be even.

<Singulation Step>

As illustrated in FIG. 8, in a singulation step, the rod-like substrate 1V is singulated into individual image pickup apparatuses 1.

The manufacturing method according to the present embodiment enables effective manufacturing of small-size image pickup apparatuses 1. In other words, the manufacturing method according to the present embodiment provides high productivity.

<Second Embodiment>

Next, an image pickup apparatus 1A according to a second embodiment of the present invention and a method for manufacturing the image pickup apparatus 1A will be described. The image pickup apparatus 1A according to the present embodiment and the method for manufacturing the image pickup apparatus 1A are similar to the image pickup apparatus 1 according to the first embodiment and the method for manufacturing the image pickup apparatus 1, and thus, components that are the same as those of the first embodiment are provided with reference numerals that are the same as those of the first embodiment and a description thereof will be omitted.

Figure 9:
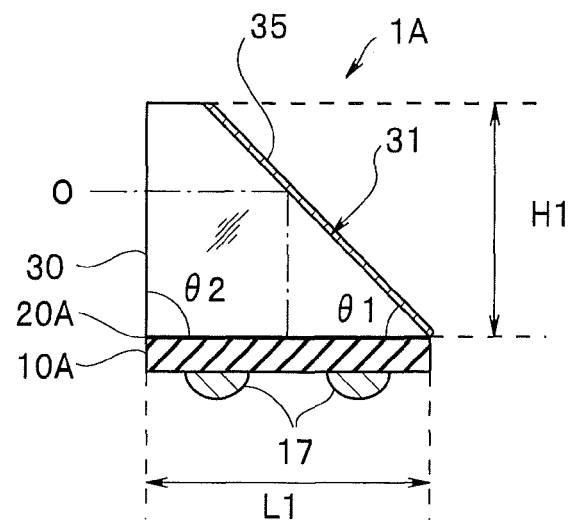
FIG. 9 is a cross-sectional structural diagram illustrating an image pickup apparatus according to a second embodiment.

As illustrated in FIG. 9, no air gap is formed in a bonding layer 20A in the image pickup apparatus 1A. This is because an image pickup device includes no microlens. Thus, the bonding layer 20A is easy to fabricate compared to the bonding layer 20 that requires patterning.

Furthermore, the image pickup apparatus 1A includes a reflective film 35 including a metal thin film on an inclined surface 31. The reflective film 35 enhances a reflection efficiency of the reflective surface of the prism. Provision of the reflective film 35 on the reflective surface of the prism enables observation of a bright image. The reflective film 35 is formed by, e.g., vapor deposition or sputtering using a metal film with high reflectivity such as aluminum or silver. Furthermore, it is preferable to form a protection film including, e.g., $SiO_2$ outside the reflective film 35, for prevention of oxidation of the metal film. From the perspective of productivity, it is preferable that the reflective film 35 and the protection film be formed at the stage of rod-like substrates 1V.

The inclined surface 31 having the reflective film 35 thereon provides enhanced light reflection efficiency. In other words, the image pickup apparatus 1A efficiently forms an image of a light beam from an image pickup optical system on an image pickup device 13 because of smaller reflection loss at the inclined surface 31.

In the case of the image pickup apparatus 1A, rod-like substrates 1V are fabricated by a step-cut method. In other words, in a prism fabricating step, a blade 2 forms grooves only in a glass substrate 30W. In other words, bottom portions of the grooves do not reach an image pickup device substrate. Thus, after the prism fabricating step, a bonded substrate 1W is not separated into rod-like substrates 1V and remains in a state of a wafer in which the groove portions 3 are formed. Then, by means of dicing processing in a separation step after the prism fabricating step, the bonded substrate 1W is separated into rod-like substrates 1V. Note that side faces of an image pickup device substrate portion 10A are perpendicular to the first principal surface 11.

Also, it is possible that: first, a V-shaped groove including two reflective surfaces are formed using a blade with opposite surfaces each having an inclination of 45 degrees; and a bottom portion of the V-shaped groove and a separation part between two rod-like substrates are separated by a perpendicular surface, respectively.

Note that as illustrated in FIG. 9, as with the image pickup apparatus 1, a chip size L1 of the image pickup apparatus 1A is set to be substantially equal to a height H1 of the prism, that is, a thickness of a cover glass portion 30. In other words, in the case of the image pickup apparatuses 1 and 1A, a prism is not disposed on the cover glass portion 30 but a prism is fabricated by processing the cover glass portion 30, enabling fabrication of a prism with a requisite minimum size.

Note that as illustrated in, e.g., FIG. 1, in the case of the image pickup apparatuses 1 and 1A, in the prism fabricating step, parts of the upper face of the glass substrate 30W are not subjected to the processing for providing the inclined surfaces 31. In other words, the prism in each of the image pickup apparatuses 1 and 1A includes an upper face 34. This is intended to facilitate handling of the rod-like substrates 1V and the image pickup apparatuses 1 and 1A. For example, in the case of the image pickup apparatus 1 including the upper face 34, when the image pickup apparatus 1 is mounted on a wiring board, the mounting can be performed with reference to the upper face 34 parallel to the lower face 33, that is, the first principal surface 11. Furthermore, the image pickup apparatus 1 having the above-described structure is resistant to, e.g., chipping compared to a case where the image pickup apparatus 1 includes an acute-angled glass end face.

<Third Embodiment>

Figure 10:
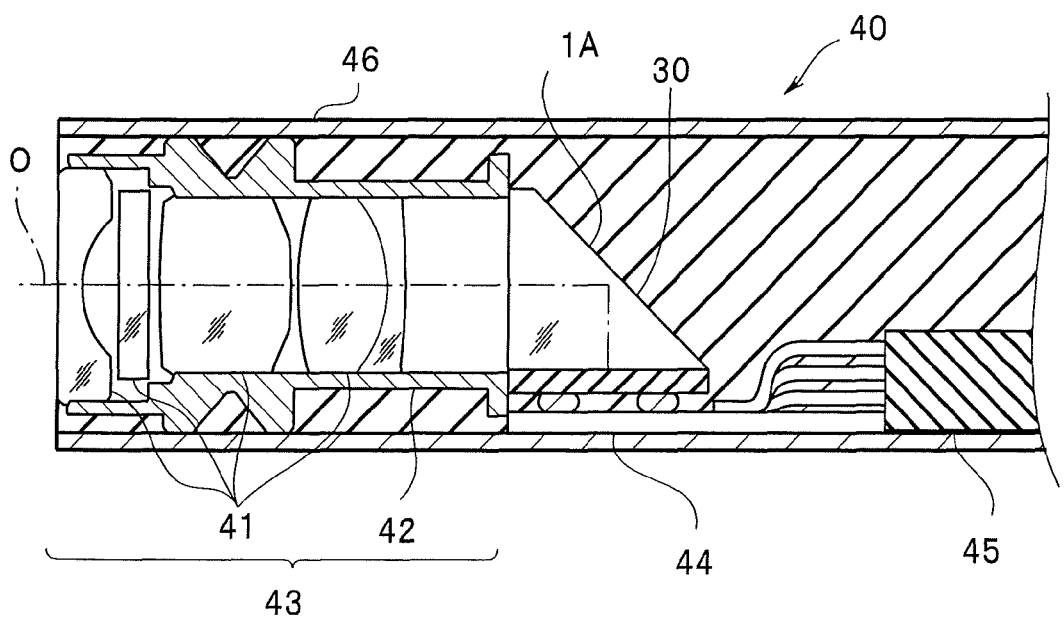
FIG. 10 is a cross-sectional structural diagram illustrating an endoscope including an image pickup apparatus according to a third embodiment.

Next, an endoscope 40 including the image pickup apparatus 1A will be described as a third embodiment. FIG. 10 is a diagram illustrating a cross-sectional structure of a distal end portion of an insertion portion of the endoscope 40. As illustrated in FIG. 10, in the endoscope 40 with the image pickup apparatus 1A incorporated in the distal end portion of the insertion portion, an image pickup optical system 43 including a plurality of lens portions 41 and an image pickup apparatus 1A are fixed by a barrel portion 46. The inside of the barrel portion 46 is charged with a non-conducive resin filler having high thermal conductivity. A cable 45 is connected to a wiring board 44 on which the image pickup apparatus 1A is mounted via back-face electrodes 17.

Anterior to a cover glass portion 30, which provides a prism in the image pickup apparatus 1A, the image pickup optical system 43 is fixed after alignment (optical position adjustment). Thus, an optical path of an optical image from the image pickup optical system 43 is converted by 90 degrees by an inclined surface 31, whereby the optical image is formed on a pixel area of the image pickup device 13.

In the endoscope 40 including, e.g., the image pickup apparatus 1A in the distal end portion of the insertion portion, the cover glass portion 30, which is essential as a protective member, is a right angle prism having an optical path conversion function, and thus, the endoscope 40 enables reduction in diameter and is less invasive. Furthermore, the endoscope 40 is low in cost because of the high productivity.

The present invention is not limited to the above-described embodiments and modifications and the like, and various modifications and alternation and the like are possible without departing from the spirit of the present invention. For example, the reflective film described in the second embodiment may be used in the image pickup apparatus 1 according to the first embodiment, or the image pickup apparatus 1 according to the first embodiment may be installed in the endoscope according to the third embodiment.

What is claimed is:

1. A method comprising:
fabricating an image pickup device substrate comprising a plurality of image pickup devices on a first principal surface of the image pickup device substrate and a plurality of back-face electrodes on a second principal surface of the image pickup device substrate, wherein the plurality of back-face electrodes are connected to the plurality of image pickup devices via a plurality of wiring portions;
fabricating a bonded substrate by bonding a transparent substrate to the first principal surface of the image pickup device substrate;
after fabricating the bonded substrate, fabricating a plurality of optical path conversion elements by forming one or more surfaces in the transparent substrate, wherein the one or more surfaces define respective optical paths of light towards respective ones of the plurality of image pickup devices; and
singulating the bonded substrate into individual image pickup apparatuses, wherein each of the individual image pickup apparatuses comprises at least one of the plurality of image pickup devices and at least one of the plurality of optical path conversion elements.

2. The method according to claim 1,
wherein the fabrication of the plurality of optical path conversion elements comprises forming a plurality of right angle prisms by foaming a perpendicular surface and an inclined surface in the transparent substrate, and
wherein the perpendicular surface is perpendicular to the first principal surface of the image pickup device substrate, and the inclined surface is inclined by 45 degrees relative to the first principal surface of the image pickup device substrate.

3. The method according to claim 2, wherein the fabrication of the plurality of optical path conversion elements further comprises dicing the bonded substrate into a plurality of rod-like substrates, wherein each of the plurality of rod-like substrate comprises a plurality of the image pickup devices.

4. The method according to claim 3, further comprising grinding the inclined surface and the perpendicular surface.

5. The method according to claim 2, further comprising forming a reflective film on the inclined surface.

6. The method according to claim 1, wherein the fabrication of the bonded substrate comprises bonding each of regions in peripheries of the image pickup devices to the transparent substrate via a bonding layer to form an air gap between each of regions where the image pickup devices are formed and the transparent substrate.

* * * * *